US00PP31239P2

(12) United States Plant Patent
Hansen

(10) Patent No.: US PP31,239 P2
(45) Date of Patent: Dec. 17, 2019

(54) ***PHLOX* PLANT NAMED 'MAGENTA SPRITE'**

(50) Latin Name: ***Phlox* hybrid**
Varietal Denomination: Magenta Sprite

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 16/350,550

(22) Filed: Nov. 30, 2018

(51) Int. Cl.
*A01H 5/02* (2018.01)
*A01H 6/70* (2018.01)

(52) U.S. Cl.
USPC ..... Plt./320

(58) Field of Classification Search
USPC ..... Plt./320
See application file for complete search history.

*Primary Examiner* — Susan McCormick Ewoldt

(57) ABSTRACT

A new and unique cultivar of hybrid creeping phlox named *Phlox* 'Magenta Sprite' multi-stemmed, short, upright, slowly-spreading habit with clean, green, glossy, lanceolate to linear leaves with exceptional powdery mildew resistance. Flowers are magenta pink with dark purple markings at center, nearly covering the top of the plant in peak flowering season about one week later than typical *Phlox subulata*. 'Magenta Sprite' is especially useful as a containerized plant and for the flower garden as an specimen or en masse.

1 Drawing Sheet

Botanical classification: *Phlox* hybrid.
Variety denomination: 'Magenta Sprite'.

STATEMENT REGARDING PRIOR DISCLOSURES UNDER 37 CFR 1.77(b)(6)

The first public disclosure of the claimed plant, in the form of a sale, was made by Walters Gardens, Inc. on Jul. 9, 2018. Prior to that, on Dec. 1, 2017 the claimed plant was displayed with photographs and brief description on a website of Walters Gardens, Inc., who obtained the plant and all information relating thereto, from the inventor. No plants of *Phlox* 'Magenta Sprite' have been sold, in this country or anywhere in the world, nor has any disclosure of the new plant been made, more than one year prior the filing date of this application, and such sale or disclosure within one year was either derived directly or indirectly from the inventor.

BACKGROUND OF THE INVENTION

The present invention relates to a new and distinct cultivar of hybrid creeping *Phlox* plant, known as *Phlox* 'Magenta Sprite' and will be referred to hereafter by its cultivar name or the "new plant". The new plant was the result of a cross made by the inventor between *Phlox subulata* 'Emerald Pink' (not patented) as the female or seed parent and an unnamed selection of *Phlox procumbens* as the male or pollen parent performed at a wholesale perennial nursery in Zeeland, Mich. on Mar. 4, 2014. The new plant was given the breeder code 14-212-3 prior to naming and throughout subsequent evaluations at the same nursery. 'Magenta Sprite' has been asexually propagated by stem cuttings in the greenhouses at the same nursery in Zeeland, Mich. since 2016. The unique characteristics of the new plant have been found to be reproducible and stable in successive generations of asexually propagated plants and the resultant plants have been found to be identical to the original selection.

BRIEF SUMMARY OF THE PLANT

*Phlox* 'Magenta Sprite' is unique from its parents and all other hybrid creeping *Phlox* or other *Phlox* known to the inventor. 'Emerald Pink' differs by its lighter pink-colored flowers, the plants are shorter in habit, and the growth rate faster and less manageable in the landscape. The new plant has broader leaves and the habit is taller with wider and more ovate and leaves than 'Emerald Pink'. The male parent has broader foliage and the flowers are more mauve pink, the habit is more loose and open and the stems are more pubescent. The closest comparison cultivars known to the inventor are the copending application Ser. No. 16/350,549 *Phlox* 'Rose Sprite', 'PPPHL0604' U.S. Plant Pat. No. 23,703 ('Britney'), 'PPPHL07101' U.S. Plant Pat. No. 24,007 ('Lindsay'), 'PHL090201' U.S. Plant Pat. No. 26,854, 'PPPHL07301' U.S. Plant Pat. No. 23,702 ('Angelina'), 'PPPH07201' U.S. Plant Pat. No. 23,705 ('Paris') and 'PHL090401' U.S. Plant Pat. No. 26,852 ('Levine'). 'Rose Sprite' has rose pink flowers with white center or eye. 'PPPHL0604' is taller in habit, has flower color that begin a bright pink with white center eye and lacks dark purple markings near center. 'PPPHL07101' is slightly taller in habit, the petals begin a strong purplish red and lack the center purple markings. 'PPPHL07301' is taller in habit and has flowers that have a near-white eye zone and petals of a medium purple. 'PHL090201' has a slightly taller habit, the flower petals are narrower and dark lavender colored. 'PPPH07201' has slightly taller habit and the flowers are violet-blue with a dark eye. 'PHL090401' has slightly taller habit and the flowers are lavender with narrower petals.

'Magenta Sprite' differs from all other phlox known to the inventor in the following repeatedly observed traits in combination:

1. Plants of short mounded habit, slowly spreading by short rhizomes, producing clean, glossy, clean green, lanceolate to linear leaves;
2. Showing exceptional powdery mildew resistance;
3. Multiple branched, stems produce rounded mounds of flowers starting in mid-spring;
4. Faintly-sweet fragrant flowers on mounded stems of about 18.0 cm tall;
5. Flowers have magenta-pink faces with dark purple markings in center and without white center or halo zones;
6. Flower color show little to no change in color prior to dehiscence;
7. Flowers densely cover nearly the entire top of the plant;
8. Flowering about one week after typical *Phlox subulata* cultivars.

BRIEF DESCRIPTION OF THE DRAWINGS

The photographs of the new plant demonstrate the unique traits of 'Magenta Sprite' and the overall appearance of the plant at two-years-old grown in a full-sun trial garden in Zeeland, Mich. The colors are as accurate as reasonably possible with color reproductions. Variation in ambient light spectrum, source and direction may cause the appearance of minor variation in color.

DETAILED BOTANICAL DESCRIPTION

Figure 1:
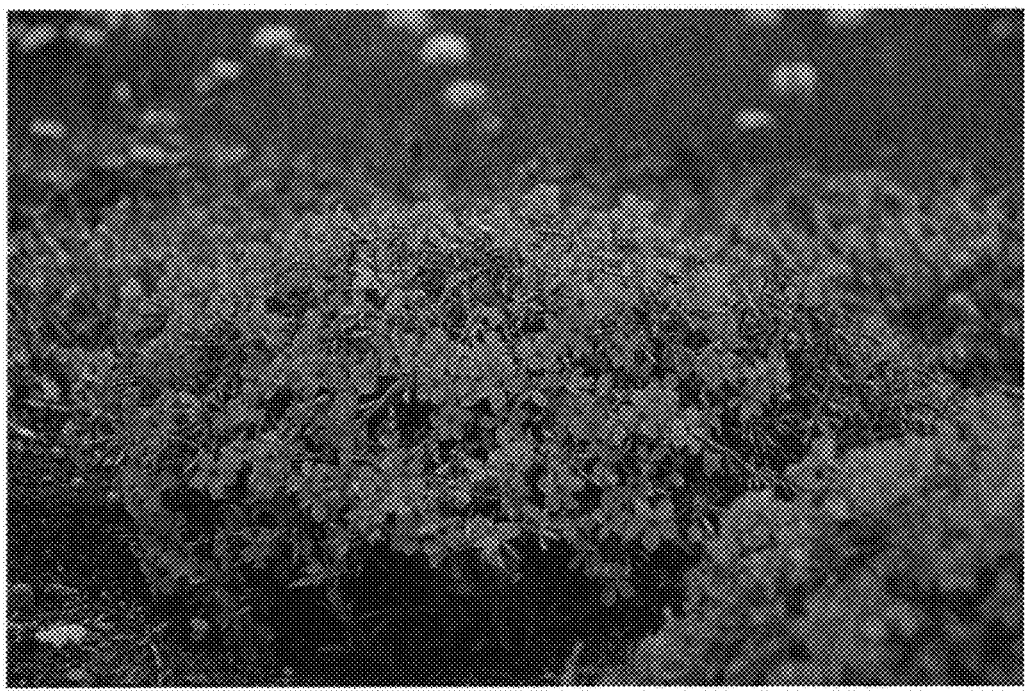
FIG. 1 shows the habit of the new plant in peak flower.
Figure 2:
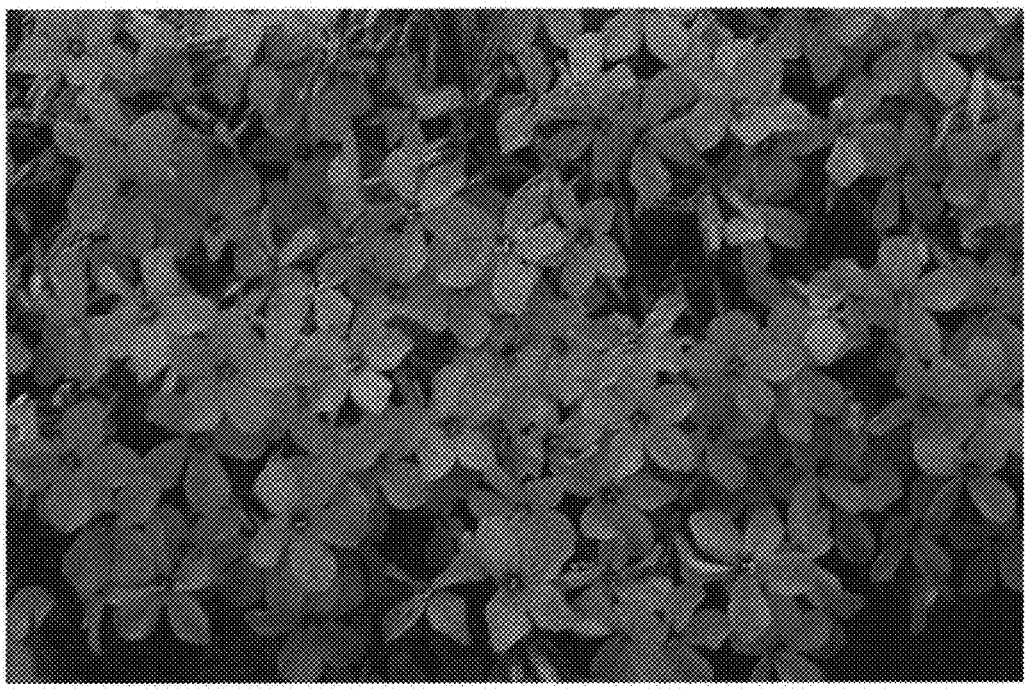
FIG. 2 shows a close-up of the flowers of different ages and buds.

The following descriptions and color references are based on the 2015 edition of The Royal Horticultural Society Colour Chart except where common dictionary terms are used. *Phlox* 'Magenta Sprite' has not been observed under all possible environments. The phenotype may vary slightly with different growing environments such as temperature, light, fertility, soil pH, moisture and maturity levels, but without any change in the genotype. The following observations and size descriptions are based on two-year-old plants in the full-sun trial garden of a wholesale perennial nursery in Zeeland, Mich. with supplemental fertilizer and water as needed.

Botanical classification: *Phlox* hybrid;

Parentage: Female or seed parent *Phlox subulata* 'Emerald Pink' and the male or pollen parent an unnamed selection of *Phlox procumbens;*

Plant habit: Densely-mounded, winter-hardy, herbaceous perennial, producing branched stems and early spring flowering; with foliage to about 9.0 cm tall and about 36.0 cm wide; densely flowering about one week after typical *Phlox subulata* cultivars and continuing for about 4 weeks;

Propagation: Stem cuttings; rooting in about 14 days;

Time to produce finished crop in 3.8 liter pots: About 12 to 14 weeks; moderate rate of growth;

Root: Primary roots to about 1.0 mm thick; secondary fibrous and freely branching; color creamy white to tan depending on soil type and root stage of development;

Leaves: Simple; opposite; lanceolate to linear; entire margin; narrowly acute apex; truncate base; sessile; slightly folded;

Leaf size: To about 29.0 mm long by about 6.0 mm wide; average about 18.0 mm long by about 5.0 mm wide;

Leaf surfaces: Lustrous and sparsely puberulent adaxial and puberulent abaxial;

Leaf color expanding: Adaxial nearest RHS 143A distally and RHS 145A proximally, and abaxial nearest RHS 144A distally and between RHS 145B and RHS 145A proximally;

Leaf color at flowering: Adaxial and abaxial base nearest RHS 145B and adaxial proximally nearest RHS 137A and abaxial proximally nearest RHS 145B;

Foliage fragrance: None detected;

Veins: Pinnate; glabrous adaxial and abaxial; midrib about 0.5 mm wide at base, slightly sunken adaxial and raised abaxial; color same as surrounding leaf tissue;

Petiole: Leaves sessile;

Stems: Cylindrical; flexible; strong; pubescent; proximally rosulate and distally decussate; average about 9.0 cm long and 2.5 mm diameter at base;

Stem color: Lower portion covered with leaves, distally nearest RHS N186C;

Nodes: About six per stem in branched peduncle region and 30 to 40 in lower portion; average internode length about 0.5 cm;

Node color: Nearest RHS N186C;

Inflorescence: A loosely-branched compound corymb of about 24 flowers; about 8.0 cm long and 6.0 cm across;

Flowers: Perfect; salverform with flat face and long fused corolla tube; actinomophic; typically with five petals; attitude upright to outwardly;

Flower size: About 22.0 mm across face and 19.0 mm long to exserted stigma; corolla tube about 14.0 mm long and about 2.5 mm diameter below face;

Flower longevity: About 5 days; self-cleaning;

Flower fragrance: Faintly sweet;

Buds one to two days prior to opening: Narrowly oblanceolate, to nearly clavate; acute apex with convolute petals; base fused; about 22.0 mm long and 2.5 mm diameter in tube base and swollen to 3.0 mm diameter toward apex of convolute petals;

Bud color: Exposed petals nearest RHS N77D and basal 2.0 mm nearest RHS 145D;

Petals: Five; limb obtuse, apex rounded and emarginate notched to 0.5 mm deep; base fused into tube; margin entire; abaxial limb glabrous and tube micro-puberulent, adaxial limb glabrous;

Petal size: Basal 14.0 mm fused into corolla tube, to a diameter of about 2.5 mm; limb face about 9.0 mm across, and face about 11.0 mm long; nearly imbricate toward center;

Petal color: Adaxial face center nearest RHS N74B with two dark purple marks of nearest RHS 77A toward center, distally nearest RHS NN74B; abaxial limb nearest RHS NN74D; adaxial corolla tube base nearest RHS 155D and distally nearest RHS N79D; abaxial base between RHS 157D and RHS 155D and distally nearest RHS N81B;

Androecium:

*Filaments.*—Typically five; adnate to adaxial inner corolla at various distances of 10.0 mm to 15.0 mm from base; free in terminal 0.5 mm; color nearest RHS NN155D.

*Anther.*—Five; oblong elliptic; basifixed; longitudinal; about 1.2 mm long by 0.7 mm wide; color nearest RHS 23B.

*Pollen.*—Abundant; color nearest RHS N163C.

Gynoecium: One pistil per flower; to about 18.0 mm long; superior;

*Style.*—Cylindrical; about 16.0 mm long and about 0.2 mm diameter; color nearest RHS 158B with blush of nearest RHS 183C.

*Stigma.*—Trifurcate in the distal 1.5 mm, less than 0.2 mm in diameter; persistent after flower abscission; color nearest RHS 8C.

*Ovary.*—Superior; globose; about 1.5 mm long and 2.0 mm diameter; color nearest RHS 143A.

Calyx: Tubular to campanulate; adpressed to corolla tube proximally and slightly reflexed distally; to about 9.0 mm long and 8.0 mm wide at apex;

Sepals: Five; linear; narrowly acute apex, margin entire; basal 4.0 mm fused; surface matte and glandular to puberulent abaxial, lustrous and glabrous adaxial; individually about 9.0 mm long and 1.0 mm wide;

Sepal color: Abaxial nearest RHS 137D; adaxial nearest RHS 141B;

Peduncle: Pubescent; flexible, strong, mostly upright; cylindrical; flowering portion about 6.0 cm long and 2.0 mm diameter at base of flower branches; branches to about 5.0 cm long and 2.0 mm diameter at base; typically five flowers per branch;

Peduncle color: Nearest blend between of RHS 183A and RHS N186C;

Pedicel: Terete; glabrous; to about 6.0 mm long and 1.0 mm diameter;

Pedicel color: Nearest RHS 146B with strong blush nearest RHS 183C;

Fruit and seeds have not yet been observed;

Hardiness and culture: The new plant grows best with plenty of moisture and adequate drainage; prefers full sun but tolerates light shade; is hardy to at least from USDA zone 3 through 8.

Disease and pest resistance: *Phlox* 'Magenta Sprite' demonstrated the excellent resistance to powdery mildew caused by *Erysiphe cichoracearum* under conditions of intense pressure that would normally show symptoms.

I claim:

1. A new and distinct cultivar of hybrid phlox plant named *Phlox* 'Magenta Sprite', as herein described and illustrated.

* * * * *